US010238640B2

(12) United States Patent
Dickerson et al.

(10) Patent No.: US 10,238,640 B2
(45) Date of Patent: Mar. 26, 2019

(54) PHARMACEUTICAL SUSPENSION COMPOSITION

(71) Applicant: Wyeth LLC, New York, NY (US)

(72) Inventors: Jay Dickerson, Midlothian, VA (US); William Mark, Glen Allen, VA (US); Annabelle Trimmer, Manakin-Sabot, VA (US); David Jaeger, Chester, VA (US); Amanda Alley, Midlothian, VA (US)

(73) Assignee: Wyeth LLC, New York, NY (US)

( * ) Notice: Subject to any disclaimer, the term of this patent is extended or adjusted under 35 U.S.C. 154(b) by 0 days.

(21) Appl. No.: 15/349,101

(22) Filed: Nov. 11, 2016

(65) Prior Publication Data

US 2017/0065567 A1    Mar. 9, 2017

Related U.S. Application Data

(60) Continuation of application No. 14/165,887, filed on Jan. 28, 2014, now abandoned, which is a continuation of application No. 12/403,081, filed on Mar. 12, 2009, now abandoned, which is a division of application No. 10/852,946, filed on May 25, 2004, now abandoned.

(51) Int. Cl.
| A61K 9/00 | (2006.01) |
| A61K 9/10 | (2006.01) |
| A61K 31/00 | (2006.01) |
| A61K 45/06 | (2006.01) |
| A61K 47/10 | (2017.01) |
| A61K 47/12 | (2006.01) |
| A61K 47/18 | (2017.01) |
| A61K 47/26 | (2006.01) |
| A61K 47/36 | (2006.01) |
| A61K 47/38 | (2006.01) |
| A61K 31/137 | (2006.01) |
| A61K 31/192 | (2006.01) |
| A61K 31/4402 | (2006.01) |

(52) U.S. Cl.
CPC ........ *A61K 31/4402* (2013.01); *A61K 9/0053* (2013.01); *A61K 9/0095* (2013.01); *A61K 9/10* (2013.01); *A61K 31/00* (2013.01); *A61K 31/137* (2013.01); *A61K 31/192* (2013.01); *A61K 45/06* (2013.01); *A61K 47/10* (2013.01); *A61K 47/12* (2013.01); *A61K 47/183* (2013.01); *A61K 47/26* (2013.01); *A61K 47/36* (2013.01); *A61K 47/38* (2013.01)

(58) Field of Classification Search
None
See application file for complete search history.

(56) References Cited

U.S. PATENT DOCUMENTS

| 4,145,440 | A | | 3/1979 | Fitch et al. |
| 4,226,848 | A | | 10/1980 | Nagai et al. |
| 4,250,163 | A | | 2/1981 | Nagai et al. |
| 4,427,681 | A | | 1/1984 | Munshi |
| 4,871,733 | A | | 10/1989 | Sunshine et al. |
| 4,975,465 | A | | 12/1990 | Motola et al. |
| 5,024,997 | A | * | 6/1991 | Motola ............... A61K 9/0095 514/570 |
| 5,272,137 | A | | 12/1993 | Blase et al. |
| 5,409,907 | A | | 4/1995 | Blase et al. |
| 5,458,879 | A | | 10/1995 | Singh et al. |
| 5,494,681 | A | * | 2/1996 | Cuca ................... A61K 9/1617 424/484 |
| 5,658,919 | A | | 8/1997 | Ratnaraj et al. |
| 5,688,529 | A | | 10/1997 | Lidgate et al. |
| 5,759,579 | A | | 6/1998 | Singh et al. |
| 6,184,220 | B1 | | 2/2001 | Turck et al. |
| 6,190,701 | B1 | | 2/2001 | Roser et al. |
| 6,287,592 | B1 | | 9/2001 | Dickinson |
| 6,319,513 | B1 | | 11/2001 | Dobrozsi |
| 6,475,539 | B1 | * | 11/2002 | DeWille ............... A23L 2/38 426/573 |
| 6,515,008 | B1 | | 2/2003 | Tiongson et al. |
| 6,890,558 | B2 | | 5/2005 | Bougaret et al. |

(Continued)

FOREIGN PATENT DOCUMENTS

| EP | 298740 | 1/1989 |
| EP | 298740 B1 | 1/1989 |

(Continued)

OTHER PUBLICATIONS

Austrian Search Report dated Sep. 17, 2005 in counterpart foreign application in Turkey under patent application No. TR2005/01948.

(Continued)

*Primary Examiner* — Robert A Wax
*Assistant Examiner* — Caralynne E Helm
(74) *Attorney, Agent, or Firm* — Paula K. Davis; Jeffrey M. Gold

(57) ABSTRACT

An aqueous oral liquid pharmaceutical composition system with reduced propensity for agglomeration and phase separation which is particularly amendable to the suspension of one or more pharmaceutical actives that are substantially insoluble in water. The oral liquid pharmaceutical composition may further comprise pharmaceutical actives that are soluble in water and dissolve in the aqueous medium. In the composition of the invention both suspended and any dissolved active agents are distributed homogeneously.

3 Claims, No Drawings

(56) References Cited

U.S. PATENT DOCUMENTS

| | | | |
|---|---|---|---|
| 2002/0028794 A1* | 3/2002 | Brubaker | A61K 9/0095 514/177 |
| 2002/0034540 A1 | 3/2002 | Price | |
| 2003/0032600 A1* | 2/2003 | Ulrich | A61K 9/0095 514/2.3 |
| 2003/0108575 A1* | 6/2003 | Lu | A61K 9/0095 424/400 |
| 2003/0118654 A1* | 6/2003 | Santos | A61K 9/0095 424/486 |
| 2003/0191192 A1 | 10/2003 | Venus et al. | |
| 2004/0038867 A1* | 2/2004 | Still | A61K 47/60 530/303 |
| 2004/0091507 A1 | 5/2004 | Gelotte et al. | |
| 2004/0147606 A1* | 7/2004 | Onuki | A61K 9/0095 514/561 |
| 2004/0258716 A1* | 12/2004 | Gao | A61K 9/0056 424/400 |
| 2008/0139528 A1* | 6/2008 | Pujara | A61K 9/0095 514/210.05 |

FOREIGN PATENT DOCUMENTS

| | | | |
|---|---|---|---|
| EP | 298740 | 11/1989 | |
| EP | 390369 | 10/1990 | |
| EP | 390369 B1 | 10/1990 | |
| EP | 556057 | 8/1993 | |
| EP | 556057 B1 | 8/1993 | |
| EP | 620001 | 10/1994 | |
| EP | 620001 A1 | 10/1994 | |
| EP | 843998 | 5/1998 | |
| EP | 843998 B1 | 5/1998 | |
| WO | WO-9858640 A1 * | 12/1998 | A61K 31/19 |
| WO | WO-02096406 A1 * | 12/2002 | A61K 9/0095 |

OTHER PUBLICATIONS

He Wen et al., "Preparation and Study of Suspension of Ibuprofen and Pseudoephodrine Hydrochloride", Zhongguo Yiyuan Yaoxue Zazhi—Chinese Journal of Hospital Pharmacy, Zhongguo Yao Xuehui Wuhan Fenhui, Wuhan, CN, vol. 19, Jan. 1, 1999, pp. 584-587, XP00152211, ISSN: 1001-5213 (Citation D4 in PCT application); abstract translated.

Anonymous, Center for Drug Evaluation and Research, Application No. 21-373, www.accessdata.fda.gov, Apr. 18, 2002, XP55023723, available at https://www.accessdata.fda.gov/drugsatfda_docs/nda/2002/21-373_Ibuprofen%20Pseudoephedrine_biopharmr.pdf.

Anonymous, Children's Advil Cold label, Application No. 21-373, www.accessdata.fda.gov, Apr. 18, 2002, XP55023727; available at https://www.accessdata.fda.gov/drugsatfda_docs/nda/2002/21-373_Ibuprofen%20Pseudoephedrine_pmtlbl.pdf.

* cited by examiner

PHARMACEUTICAL SUSPENSION COMPOSITION

This application is a continuation of application Ser. No. 14/165,887, filed on Jan. 28, 2014, which is a continuation of application Ser. No. 12/403,081, filed on Mar. 12, 2009, which is a division of application Ser. No. 10/852,946 filed on May 25, 2004, the entire disclosure of which is hereby incorporated by reference.

Orally administered pharmaceutical compositions are provided to patients in many dosage forms, including solid forms such as capsules, caplets or tablets and liquid forms such as solutions, emulsions or suspensions. Pharmaceutical compositions administered in solid form are usually intended to be swallowed whole. Children, older persons and many other persons including disabled or incapacitated patients often have trouble swallowing tablets or capsules. For many such patients, including pediatric and geriatric patients, a liquid dose form is preferable because of the ease with which it may be swallowed.

FIELD OF INVENTION

Background of Invention

Pharmaceutically acceptable liquid excipient suspension systems have been described in the literature. For example, in U.S. Pat. No. 5,759,579, Singh et al. describe a xanthan gum and hydroxypropylmethylcellulose liquid excipient for suspending solid pharmaceutically active compounds. Blasé et al. in U.S. Pat. Nos. 5,272,137 and 5,409,907 describe and claim a liquid suspension system for the substantially water soluble pharmaceutical active, acetaminophen.

Although such suspensions are known, the known systems frequently manifest the undesirable properties of irreversible agglomeration and/or phase separation particularly if a pharmaceutical active with a limited solubility in water is used. Hence, it would be desirable to have a liquid excipient suspension system with reduced propensity for occurrence of irreversible agglomeration and/or phase separation that is suitable for the suspension of pharmaceutical actives substantially insoluble in water.

SUMMARY OF THE INVENTION

The invention is directed to an oral liquid pharmaceutical composition comprising a suspending system which comprises in a preferred embodiment an aqueous composition, which includes about 0.1 g/100 mL to about 1.0 g/100 mL xanthan gum and about 0.5 g/100 mL to about 3.0 g/100 mL microcrystalline cellulose/carboxymethylcellulose sodium in an aqueous base (or "aqueous medium") and at least one pharmaceutical active (also referred to herein as "at least one pharmaceutical active compound" or "at least one first pharmaceutical active"), that is substantially insoluble in water (or the aqueous base). The suspending system is also referred to herein as an "aqueous based suspending system" or an "aqueous composition".

The pharmaceutical active is suspended in the aqueous composition and a density adjusting agent is employed to balance or match the true density of the suspended ingredients (typically the pharmaceutical active) with the specific gravity of the suspending medium. In an exemplary embodiment, the density adjusting agent comprises about 10 g/100 mL to about 50 g/100 mL glycerin and about 10 g/100 mL to about 50 g/100 mL sorbitol. Alternatively, conventional sugars and/or other polyols may be used for density adjusting. However, in some embodiments it is preferable to prepare a sugar free composition, avoiding the use of conventional sugars. Optionally, about 0.1 g/100 mL to about 1.5 g/100 mL of a surface modifying agent such as a surfactant may be included in the liquid pharmaceutical composition. The pharmaceutical active that is substantially insoluble in the aqueous composition may comprise ibuprofen, naproxen, ketoprofen or loratadine, or a mixture thereof, for example.

In one embodiment the pharmaceutical composition may further comprise at least one second pharmaceutical active which is soluble in the aqueous composition and whereby the at least one second pharmaceutical active remains in solution in the aqueous medium. The second pharmaceutical active may include one or more of pseudoephedrine, chlorpheniramine, dextromethorphan, brompheniramine, guaifenesin and diphenhydramine, for example.

The invention provides a method of preparing an oral liquid pharmaceutical composition comprising: preparing suspending system, suspending at least one substantially insoluble pharmaceutical active in the suspending system and matching the true density of the substantially insoluble pharmaceutical active with the specific gravity of the aqueous medium. The suspending system may comprise an aqueous composition which includes about 0.1 g/100 mL to about 0.5 g/100 mL xanthan gum and about 0.5 g/100 mL to about 3.0 g/100 mL microcrystalline cellulose/carboxymethylcellulose sodium and an aqueous medium. In some embodiments the method may further comprise dissolving at least one soluble pharmaceutical active in the aqueous medium and/or adding a surface modifying agent to the pharmaceutical composition.

DETAILED DESCRIPTION OF THE INVENTION

The invention provides an oral (and aqueous) liquid pharmaceutical composition system with reduced propensity for irreversible agglomeration and phase separation and is particularly amenable to the suspension of one or more pharmaceutical actives that are substantially insoluble in water. The oral liquid pharmaceutical composition may further comprise pharmaceutical actives that are soluble in water and which dissolve in the aqueous medium. In the composition of the invention both suspended and any dissolved components of the composition are distributed substantially homogeneously. The pharmaceutical composition comprises a suspending system, one or more suspended pharmaceutical actives and a density adjusting agent. The suspending system is based on a thixotropic gum system in an aqueous medium where sufficient shear (upon shaking) permits mobility of the suspension. In one preferred embodiment, the suspending system comprises xanthan gum and microcrystalline cellulose/carboxymethylcellulose sodium in an aqueous base. This combination yields thixotropic properties such that the viscosity of the undisturbed base increases over time. Such increase in viscosity is believed to facilitate minimization of the migration of the suspended active (or actives) upon storage over time. Upon shear (shaking), the viscosity decreases to allow easy dispensing of the drug product.

Additionally, the invention further offers the advantage that it is preferably formulated using polyols. The inventors believe, without wishing to be bound to the theory, that the use of polyols facilitates stability in the suspension by equilibrating the true density of the suspended ingredients with the specific gravity of the suspending medium. This is believed to minimize the migration of suspended pharmaceutical active over time. The preferred polyols for use in the practice of the invention are a mixture of glycerin and sorbitol. The sorbitol may be in pure form or a sorbitol solution, such as a 70% sorbitol in water solution, for example. Likewise pure glycerin, or a glycerin in water solution, such as 96% glycerin in water may be used. Conventional sugars, such as cane sugar or sucrose, fructose, or corn syrup alone or in combination with other sugars and/or polyols may be used as the density adjusting agent. However, in embodiments intended for administration to a young child or diabetic geriatric patient, avoidance of conventional sugars is preferable.

In some embodiments surface modifying agents, such as a surfactant, are used in the pharmaceutical composition to modify the surface of the suspended components. Such surface modification is believed to facilitate diminished irreversible aggregation of the suspended particles.

The aqueous-based suspending system may be used to suspend one or more pharmaceutically active compounds which are substantially insoluble in water or the aqueous medium. In some embodiments the aqueous suspending system may suspend one or more substantially insoluble pharmaceutical active compounds and further comprise one or more other pharmaceutically active compounds which are soluble in water and which are dissolved in the aqueous medium. In the pharmaceutical composition of the invention the pharmaceutical active compounds (i.e. active ingredients), both the suspended substantially insoluble active ingredients and any soluble active ingredients dissolved in the aqueous medium, are distributed to form a substantially homogeneous distribution of active ingredients in the pharmaceutical composition.

As used in this description and the appended claims, a pharmaceutical active that is substantially insoluble in the aqueous composition includes ibuprofen, ketoprofen, naproxen, celecoxib, rofecoxib, valdecoxib, nabumetone, glimepiride, diclofenac, piroxicam and meloxicam. For pharmaceutical actives not specified on this list a pharmaceutical active substantially insoluble in the aqueous composition means a pharmaceutical active designated as relatively insoluble or insoluble in water by the Merck Index.

A pharmaceutical active designated to be soluble in the aqueous composition includes fexofenadine (HCl), chlorpheniramine (maleate), brompheniramine (maleate), diphenhydramine (HCl, citrate), cetirizine (HCl), carbinoxamine (maleate), loratadine, desloratadine, guaifenesin, pseudoephedrine (HCl, sulfate), phenylpropanolamine (HCl), ephedrine (HCl, sulfate), dextromethorphan (HBr), codeine (phosphate) and hydrocodone (bitartrate). For pharmaceutical actives not specified on this list, soluble pharmaceutical active means a pharmaceutical active indicated to be soluble in water by the Merck Index.

Unless otherwise specified, amounts designated in g/100 mL means grams per 100 milliliters of the pharmaceutical composition. For example, 10 g/100 mL ibuprofen means 10 g of ibuprofen in 100 mL of the oral liquid pharmaceutical composition. A designation of mg/5 mL means milligrams per 5 milliliters of the pharmaceutical composition. For example, a designation of 10 mg/5 mL ibuprofen means 10 mg of ibuprofen would be found in 5 milliliters of the composition. The preferred dosage unit is 5 mL, to be administered to the patient as a single dosage unit or multiples thereof, based on age and weight.

The term "medium density matching" (or "density matching") means balancing the true density of the suspended components (ingredients) in the composition with the specific gravity of the suspending medium. Density matching is accomplished using a "density adjusting agent" which may be comprised of one or more components. Typically, the desired amount of suspended component and its density is determined and the amount of density adjustment agent needed to adjust the specific gravity of the medium to match the density of the suspended compound is determined by calculation. Calculations of density and specific gravity are well known to those skilled in the art. In some instances it is desirable to make density and specific gravity measurements, which are familiar to those skilled in the art, and use the information obtained to experimentally correct the amounts of components in the density adjusting agent and/or amount of water to account for deviation between theoretical amounts calculated and actual properties manifested by the composition.

In one exemplary embodiment the density matching is accomplished using the density adjusting agent of sorbitol, or a sorbitol/water solution, and glycerin, or a glycerin/water solution, in combination with adjusting the amount of water in the composition. For a representative example in which ibuprofen was the substantially insoluble pharmaceutically active agent, the desired density matching was achieved using a ratio of water:sorbitol (70% solution in water): glycerin (96% in water) of about 5.6:2:3.

In some embodiments propylene glycol may be used in combination with sorbitol and/or glycerin for density balancing. Although polyols other than conventional sugars are preferred in some embodiments of the invention, conventional sugars, mixtures of sugars or mixtures of sugars with other polyols may be used in the invention. The "density adjusting agent" comprises the component or components (typically one or more polyols), excluding water, added to achieve density matching.

"Microcrystalline cellulose/carboxymethylcellulose sodium" means a dried coprecipitated microcrystalline of cellulose and sodium carboxymethylcellulose. Microcrystalline cellulose/carboxymethylcellulose sodium is a typical example of a coprecipitate in microcrystalline cellulose which may be used in the practice of the invention.

The suspending system of the invention is an aqueous based system including xanthan gum and/or microcrystalline cellulose/carboxymethylcellulose sodium incorporated therein. While either xanthan gum or microcrystalline cellulose/carboxymethylcellulose sodium may be used alone in the practice of the invention, in a preferred embodiment the combination is used. Xanthan gums suitable for use in the present invention are high molecular weight polysaccharides such as the xanthan gum produced by *Xanthamonas capestris*, for example. Xanthan gum is an article of commerce and is available, for example, from manufacturers such as: Rhodia, Inc. under the brand name Rhodigel™ and from Kelco™, a division of Merck Rhodigel™ 80 Pharm Grade is exemplary of one specific commercial product suitable for use in the practice of the invention.

The xanthan gum is present in the liquid pharmaceutical composition in an amount of about 0.1 g/100 mL to about 1.0 g/100 mL. More preferably the xanthan gum is present in an amount of about 0.1 g/100 mL to about 0.3 g/100 mL and most preferably about 0.2 g/100 mL xanthan gum is used. It is preferable that the gum be dispersed in glycerin and hydrated in water prior to the addition of other components to the gum system.

A microcrystalline cellulose/carboxymethylcellulose sodium suitable for use in the practice of the invention is a coprecipitated microcrystalline cellulose and sodium carboxymethylcellulose. It is preferable that the microcrystalline cellulose/carboxymethylcellulose sodium comprises sodium carboxymethylcellulose in the range of from about 8 weight percent to about 19 weight percent and more preferably about 8 to about 15 weight percent sodium carboxymethylcellulose. Microcrystalline cellulose/carboxymethylcellulose sodium is commercially available, e.g., from FMC under the trademark Avicel™. Suitable Avicels™ include but are not limited to Avicel™ CL-611; Avicel™ RC-581; and Avicel™ RC-591. Avicel™ CL-611 is the preferred Avicel™ for use in the suspending system.

The oral pharmaceutical composition preferably comprises about 0.5 g/100 mL to about 3.0 g/100 mL, more preferably about 1 g/100 mL to about 2 g/100 mL, and most preferably about 1.5 g/100 mL microcrystalline cellulose/carboxymethylcellulose sodium. When used in combination with xanthan gum, it is preferable that the weight of microcrystalline cellulose/carboxymethylcellulose sodium used be about 5 to about 10 times that of the weight of xanthan gum used and more preferable that the weight of microcrystaline cellulose/carboxymethylcellulose sodium be about 7.5 times that of the weight of xanthan gum when used in combination.

The pharmaceutically active compounds useful in the practice of the present invention include non-steroidal anti-inflammatory drugs (NSAIDS), antihistamines, decongestants, antitussives, expectorants and analgesic drugs such as acetaminophen and phenacetin. Amounts of pharmaceutically active compounds incorporated are conventional dosages known to those skilled in the art. Further, for pharmaceutical compositions intended for use in the United States, amounts of pharmaceutical actives are preferably in compliance with applicable FDA regulation regarding dosage of such compounds.

Non-steroidal anti-inflammatory drugs (NSAIDS) which may be used in the practice of the invention include, but are not limited to: propionic acid derivatives such as ibuprofen, naproxen, ketoprofen, flurbiprofen, fenoprofen, suprofen, flurprofen and fenbufen; acetic acid derivatives such as tolmetin sodium, zomepirac, sulindac, and indomethacin; fenamic acid derivatives such as mefenamic acid and meclofenamate sodium; biphenyl carboxylic acid derivatives such as diflunisal and flufenisal and oxicams such as piroxicam, sudoxicam and isoxicam.

Antihistamines useful in the practice of the present invention (along with their preferred salt form) include, but are not limited to, chlorpheniramine (maleate), brompheniramine (maleate); dexchlorpheniramine (maleate), dexbrompheniramine (maleate), triprolidine (HCl), diphenhydramine (HCl), doxylamine (succinate), tripelennamine (HCl), cyproheptadine (HCl), bromodiphenhydramine (HCl), phenindamine (tartrate), pyrilamine (maleate, tannate), azatadine (maleate); acrivastine, astemizole, azelastine, cetirizine, ebastine, fexofenadine, ketotifen, carbinoxamine (maleate), desloratadine, loratadine, mizolastine and terfenadine.

Antitussives useful in the practice of the present invention (along with their preferred salt form) include, but are not limited to, caramiphen (edisylate), dextromethorphan (HBr), codeine (phosphate, sulfate) and hydrocodone.

Decongestants useful in the practice of the invention (along with their preferred salt form) include, but are not limited to, pseudoephedrine (HCl), ephedrine (HCl, sulfate), phenylephrine (bitartrate, tannate, HBr, HCl), and phenylpropanolamine (HCl).

Expectorants which may be used in the practice of the invention (along with their preferred salt form) include but are not limited to terpin hydrate, guaifenesin (glycerol, guaiacolate), potassium (iodide, citrate) and potassium guaiacolsulfonate.

Cox 2 inhibitors which may be used in the practice of the invention include celecoxib, rofecoxib and valdecoxib.

Other Pharmaceutical actives which are substantially insoluble and may be suspended in the suspending system of the invention include nabumetone, glimepiride, diclofenac, piroxicam and meloxicam.

Of the pharmaceutically active compounds described above, those which are particularly preferred are set forth below along with preferred ranges for their inclusion into the claimed pharmaceutical composition.

Ibuprofen may be used in amounts of up to about 3 grams per 100 mL. Preferably ibuprofen is present in amounts of between about 1 g/100 mL and about 3 g/100 mL. Most preferably, ibuprofen is present in amounts of about 2 g/100 mL of the pharmaceutical composition.

Naproxen may be used in amounts of about 1 g/100 mL to about 5 g/100 mL of the pharmaceutical composition. Preferably naproxen, when used in the pharmaceutical composition, is present in amounts of between about 2 g/100 mL and about 3 g/100 mL of the pharmaceutical composition.

Chlorpheniramine may be used in the pharmaceutical composition in amounts between about 0.01 g/100 mL and about 0.05 g/100 mL. Preferably chlorpheniramine, when used in the pharmaceutical composition, is present in the amount of about 0.01 g/100 mL to 0.03 g/100 mL.

Pseudoephedrine may be used in the pharmaceutical composition in amounts between about 0.1 g/100 mL and about 0.6 g/100 mL of the suspension. Preferably, pseudoephedrine, when used in the composition, is present in amounts of about 0.2 g/100 mL to about 0.4 g/100 mL of the pharmaceutical composition.

Chlorpheniramine maleate may be used in the pharmaceutical composition, preferably in the amount of about 0.01 g/100 mL to about 0.03 g/100 mL.

Brompheniramine maleate may be used in the pharmaceutical composition, preferably in the amount of about 0.01 g/100 mL to about 0.03 g/100 mL.

Dextromethorphan HBr may be used in the pharmaceutical composition, preferably in the amount of about 0.05 g/100 mL to about 0.250 g/100 mL.

Diphenhydramine may be used in the pharmaceutical composition, preferably in an amount of about 0.10 g/100 mL to about 0.40 g/100 mL.

The pharmaceutically active compounds are preferably of N.F. (National Formulary) or U.S.P. (United States Pharmacopeia) grade.

Excipients known by those skilled in the art may be useful in the practice of the present invention. Such excipients may include but are not limited to humectants such as glycerin and propylene glycol, defoaming agents, buffers, electrolytes, preservatives such as sodium benzoate and disodium edetate, sweeteners, taste masking agents and various flavoring and coloring agents. It is preferable to use "non-sugar" sweeteners, e.g. avoidance of the use of conventional sugars such as cane sugar or sucrose, and corn syrup, or fructose is preferred. Preferred sweeteners include sucralose, acesulfame K, saccharin sodium, and sorbitol. To the extent that polyols are intended for use as excipients, this use should be accounted for in the density matching e.g., addition of polyols not accounted for in the medium density matching is typically not desirable.

Examples of suitable flavoring agents include, but are not limited to, natural and artificial flavors such as mints (i.e., peppermint, etc.), menthol, cinnamon, vanilla, artificial vanilla, chocolate, artificial chocolate, bubblegum, both artificial and natural fruit flavors (i.e., cherry, grape, orange, strawberry, etc.) and combinations of two or more thereof. Flavoring agents are generally provided as a minor component of the suspension in amounts effective to provide palatable flavor to the compositions. Typically, flavoring agents are present in amounts in the range of about 0 grams to about 5 grams per 100 ml of the composition.

Preservatives useful in the present invention include but are not limited to sodium benzoate, potassium sorbate, salts of edetate (also known as salts of ethylenediaminetetraacetic acid or EDTA, such as disodium edetate), benzalkonium chloride and parabens (such as methyl, ethyl, propyl, and butyl p-hydroxybenzoic acid esters). Preservatives listed above are exemplary, but each preservative must be evaluated on an experimental basis, in each formulation to assure compatibility and efficacy of the preservative. Methods for evaluating the efficacy of preservatives in pharmaceutical formulations are known to those skilled in the art. Sodium benzoate and disodium edetate are the presently preferred preservative ingredients.

Preservatives are generally present in amounts of up to one gram per 100 ml of the pharmaceutical composition. Preferably the preservatives are present in amounts in the range of from about 0.1 g/100 mL to about 0.4 g/100 mL of the composition. Typically, the preservative sodium benzoate would be present in the range of about 0.2 g/100 mL to about 0.3 g/100 mL of the composition. Sodium benzoate is typically used in a concentration of about 0.25 g/100 ml of the composition.

Coloring agents may also be incorporated in the pharmaceutical composition to provide an appealing color to the composition. The coloring agents should be selected to avoid chemical incompatibilities with other ingredients in the suspension. Suitable coloring agents are well known to those skilled in the art.

Typically, water is added in the process of making the pharmaceutical composition in portions with various components. During the process of preparation of the pharmaceutical composition, amounts of added water are believed to be particularly important in three instances. Sufficient water should be available when soluble active ingredient(s) and soluble salts are added to permit them to dissolve, a sufficient amount of water should be available in combination with the density adjusting agent to achieve medium density matching, and sufficient water should be available to hydrate the water soluble/dispersible gums.

Preferably, the specific gravity of the liquid portion (i.e., the suspending medium) of the suspension should be balanced with the true density of the suspended actives. This may be accomplished by adding a density adjusting agent. For a typical example, a density adjusting agent comprising about 10 g/100 mL to about 50 g/100 mL glycerin and about 10 g/100 mL to about 50 g/100 mL sorbitol may be added to the pharmaceutical composition to achieve the desired density balance. In an exemplary embodiment containing ibuprofen as a substantially insoluble active, the desired balance was achieved using about 30 g/100 mL glycerin (96% in water) and 20 g/100 mL sorbitol (70% solution in water). The use of the polyol, sorbitol, is preferred in some embodiments as it also offers the additional advantage of sweetening the composition.

It will be understood by those skilled in the art that as liquids other than water are included in the liquid portion of the pharmaceutical composition, the amounts of the components including water used to balance the specific gravity of the liquid portion with the true density may need to be adjusted to achieve the desired balance.

Optionally about 0.1 g/100 mL to 1.5 g/100 mL surfactant may be added to the suspending system to further stabilize the pharmaceutical composition. The inventors believe, without wishing to be bound to the theory, that the surfactant modifies the surface of suspended actives and facilitates diminished irreversible aggregation of the suspended particles. The surfactant may be an ionic or non-ionic surfactant or mixtures thereof. Exemplary surfactants include but are not limited to polysorbates (tweens), Spans™, togats, lecithin, polyoxyethylene-polyoxypropylene block copolymers and medium chain mono/di-glycerides. In an exemplary embodiment in which ibuprofen was the active agent, polysorbate 80 was used in an amount of about 0.3 g/100 mL.

For an exemplary embodiment of the pharmaceutical composition, the pH is about 3.5 to about 4.5 and the disturbed viscosity (e.g. viscosity measured after mixing under specified conditions) at 25° C. will be about 1500 to about 4500 cps.

Example 1

The following Example discloses a pharmaceutical composition (which is, a suspension) comprising ibuprofen as a substantially insoluble active and a process for manufacturing this composition. The composition of the suspension of Example 1 is provided in Table 1 below:

TABLE 1

| Component | g/100 mL |
|---|---|
| Ibuprofen USP (40 micron particle size) | 2.00 |
| Pseudoephedrine HClHCl USP | 0.300 |
| Chlorpheniramine Maleate USP | 0.0200 |
| Xanthan Gum NF (Rhodigel 80 Pharma Grade) | 0.200 |
| Microcrystalline Cellulose/Carboxymethylcellulose Sodium NF (Avicel Type CL 611) | 1.50 |
| Polysorbate 80 NF | 0.300 |
| Glycerin 96% USP | 30.0 |
| Sorbitol Solution USP 70% | 20.0 |
| Micronized Sucralose Powder NF | 0.200 |
| Sodium Citrate USP/FCC | 0.550 |
| Sodium Benzoate NF | 0.250 |
| Edetate Disodium USP | 0.0500 |
| Citric Acid Hydrous USP | 0.750 |
| Flavor | 0.360 |
| Color | 0.0025 |
| Purified Water USP | Qs 100 mL |

As indicated in the header of Table 1, amounts are stated in grams per 100 milliliter aliquot of the final composition. Density matching was accomplished by first calculating theoretical amounts of components of density adjusting agent based on the density of the insoluble active and specific gravity of the aqueous based medicine, preparing the composition based on calculated amounts, then making experimental measurements on the composition, and making final adjustment of component amounts of density matching agents for desired matching of specific gravity of the medium with the true density of suspended component based on experimental measurements. Amounts of density matching agent components for the Example disclosed in Table 1 were determined using this approach prior to manufacture of the composition.

The composition of Example 1 was prepared by placing a portion of the glycerin in a first stainless steel mixing vessel equipped with variable speed mixer and gradually adding the xanthan gum with mixing to thoroughly disperse the xanthan gum. An aliquot of water (an amount less than the final amount of water) was added to a second stainless steel mixing vessel (main vessel) equipped with a variable speed mixer and the microcrystalline cellulose/carboxymethyl cellulose sodium was added with mixing to hydrate the microcrystalline cellulose/carboxymethyl cellulose sodium. The thoroughly mixed glycerin/xanthan gum and microcrystalline cellulose/carboxymethyl cellulose sodium/water dispersions were then combined in the main vessel with mixing. Edetate disodium was then added and mixing was continued until the composition was uniform.

Sorbitol solution (70% sorbitol in water) was placed in a third stainless steel vessel equipped with a mixer. Polysorbate 80 was added to the sorbitol solution and mixed thoroughly. Ibuprofen was then added to the sorbitol/polysorbate 80 solution and mixed thoroughly to uniformly disperse the ibuprofen.

Sodium benzoate, sodium citrate, sucralose micronized powder and coloring agents were dissolved in an aliquot of purified water and then added to the contents of the main vessel with mixing.

Following the addition of the sodium benzoate, sodium citrate, sucralose and coloring agent mixture, the sorbitol/polysorbate 80/ibuprofen dispersion was added to the contents of the main vessel with mixing.

Upon completion of transfer of the sorbitol/polysorbate 80/ibuprofen dispersion to the main vessel and mixing of the resulting composition, a citric acid solution in purified water was prepared and added to the contents of the main vessel.

Soluble actives, pseudoephedrine HCl and chlorpheniramine maleate, were dissolved in this example, in a water/glycerin mixture and then added to the contents of the main vessel with mixing. Assembly of the composition of Example 1 was completed by adding flavor to the contents of the main vessel and adding sufficient purified water to adjust batch volume to the final batch size.

After the final addition of components, mixing was continued for an additional 30 minutes with the composition being re-circulated through a 40-mesh filter. The composition was de-aerated by subjecting it to a vacuum prior to packaging and/or storage.

Example 2

The composition of Example 2 is provided in Table 2 below:

TABLE 2

| Component | g/100 mL |
| --- | --- |
| Ibuprofen USP (40 micron particle size) | 2.00 |
| Pseudoephedrine HCl USP | 0.300 |
| Dextromethorphan HBr USP | 0.150 |
| Xanthan Gum NF (Rhodigel 80 Pharma Grade) | 0.200 |
| Microcrystalline Cellulose/Carboxymethyl-cellulose Sodium NF (Avicel Type CL 611) | 1.50 |
| Propyl Gallate NF (Progallin P-Drum) | 0.00500 |
| Polysorbate 80 NF | 0.300 |

TABLE 2-continued

| Component | g/100 mL |
| --- | --- |
| Glycerin 96% USP | 30.0 |
| Sorbitol Solution USP 70% | 20.0 |
| Micronized Sucralose Powder NF | 0.200 |
| Sodium Citrate USP/FCC | 0.550 |
| Sodium Benzoate NF | 0.250 |
| Edetate Disodium USP | 0.0500 |
| Citric Acid Hydrous USP | 0.750 |
| Flavor | 0.334 |
| Color | 0.0300 |
| Purified Water USP | Qs 100 mL |

Example 2 is prepared in a manner similar to Example 1. The propyl gallate is dispersed in glycerin prior to addition of water, then combined with the soluble actives prior to addition to the main vessel. After the addition of the soluble actives and propyl gallate to the main vessel, flavor is then added followed by the adjustment of the final volume with water.

Although the foregoing invention has been described in some detail by way of illustration and examples for purposes of clarity of understanding, it will be obvious that certain changes and modifications, may be practiced within the scope of the appended claims. Modifications of the above-described modes of practicing the invention that are obvious to persons of skill in the art are intended to be included within the scope of the following claims.

We claim:

1. A thixotropic oral liquid pharmaceutical composition consisting of 0.2 g/100 mL xanthan gum; 1.5 g/100 mL microcrystalline cellulose/carboxymethylcellulose sodium; about 2 g/100 mL ibuprofen; about 28.8 g/100 mL glycerin; 20 g/100 mL sorbitol solution 70%; about 0.2 g/100 mL sucralose; 0.3 g/100 mL polysorbate; about 0.02 g/100 mL chlorpheniramine maleate; about 0.3 g/100 mL pseudoephedrine; about 0.55 g/100 mL sodium citrate; about 0.25 g/100 mL sodium benzoate; about 0.05 g/100 mL edetate disodium; about 0.75 g/100 mL citric acid; flavoring agent; coloring agent; and water.

2. A thixotropic oral liquid pharmaceutical composition consisting of about 2 g/100 mL ibuprofen; 0.2 g/100 mL xanthan gum; 1.5 g/100 mL microcrystalline cellulose/carboxymethylcellulose sodium; about 28.8 g/100 mL glycerin; 20 g/100 mL sorbitol solution 70%; about 0.55 g/100 mL sodium citrate; about 0.05 g/100 mL edetate disodium; about 0.75 g/100 mL citric acid; 0.3 g/100 mL polysorbate; about 0.25 g/100 mL sodium benzoate; about 0.2 g sucralose/100 mL; flavoring agent; and water.

3. A thixotropic oral liquid pharmaceutical composition consisting of 0.2 g/100 mL xanthan gum; about 1.5 g/100 mL microcrystalline cellulose/carboxymethylcellulose sodium; about 1 g/100 mL to about 3 g/100 mL ibuprofen; 0.3 g/100 mL polysorbate; about 0.25 g/100 mL sodium benzoate; about 0.01 g/100 mL to about 0.40 g/100 mL diphenhydramine; about 28.8 g/100 mL glycerin; about 20 g/100 mL sorbitol solution 70%; sucralose; about 0.55 g/100 mL sodium citrate; about 0.05 g/100 mL edetate disodium; about 0.75 g/100 mL citric acid; flavoring agent; and water.

* * * * *